(12) United States Patent
Pickover et al.

(10) Patent No.: US 10,603,578 B2
(45) Date of Patent: Mar. 31, 2020

(54) LOCATION-BASED AUGMENTED REALITY GAME CONTROL

(71) Applicant: International Business Machines Corporation, Armonk, NY (US)

(72) Inventors: Clifford A. Pickover, Yorktown Heights, NY (US); Komminist Weldemariam, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 217 days.

(21) Appl. No.: 15/582,718

(22) Filed: Apr. 30, 2017

(65) Prior Publication Data
US 2018/0311572 A1 Nov. 1, 2018

(51) Int. Cl.
*A63F 13/00* (2014.01)
*A63F 9/24* (2006.01)
(Continued)

(52) U.S. Cl.
CPC .......... *A63F 13/216* (2014.09); *A63F 13/212* (2014.09); *A63F 13/25* (2014.09); *G16H 10/00* (2018.01); *G16H 15/00* (2018.01); *G16H 40/63* (2018.01); *G16H 50/30* (2018.01); *A63F 2300/8082* (2013.01); *G06F 16/29* (2019.01)

(58) Field of Classification Search
CPC ...... A63F 13/212; A63F 13/216; A63F 13/65; G06T 19/006
See application file for complete search history.

(56) References Cited

U.S. PATENT DOCUMENTS

| 8,167,724 B2 | 5/2012 | Shuster |
| 8,585,476 B2 | 11/2013 | Mullen |

(Continued)

FOREIGN PATENT DOCUMENTS

| WO | 2013186636 | 12/2013 |
| WO | 2015161062 | 10/2015 |

OTHER PUBLICATIONS

Clifford A. Pickover et al., unpublished U.S. Appl. No. 15/859,539, filed Dec. 31, 2017, Location-Based Augmented Reality Game Control, pp. 1-27 plus 4 sheets of drawings.

(Continued)

*Primary Examiner* — Milap Shah
(74) *Attorney, Agent, or Firm* — Eyal Gilboa; Otterstedt, Wallace & Kammer, LLP

(57) ABSTRACT

A method and apparatus for deterring augmented reality game players from intruding on undesirable locations (e.g., high risk locations, culturally sensitive locations, locations marked by property owners). The exemplary method includes obtaining a location of a mobile device using a first sensor of the mobile device and accessing a first locational database responsive to the location of the mobile device. The exemplary method further includes retrieving from the first locational database an augmented reality object; obtaining an indication that the location of the mobile device is an undesirable location; and modifying the augmented reality object responsive to the indication that the location of the mobile device is an undesirable location. The exemplary method also includes displaying the modified augmented reality object at a display of the mobile device.

3 Claims, 4 Drawing Sheets

(51) Int. Cl.
*A63F 13/216* (2014.01)
*G16H 15/00* (2018.01)
*A63F 13/212* (2014.01)
*G16H 10/00* (2018.01)
*A63F 13/25* (2014.01)
*G16H 50/30* (2018.01)
*G16H 40/63* (2018.01)
*G06F 16/29* (2019.01)

(56) References Cited

U.S. PATENT DOCUMENTS

| | | | |
|---|---|---|---|
| 8,591,326 | B2 | 11/2013 | Shuster |
| 8,821,274 | B2 | 9/2014 | Lyons |
| 9,132,342 | B2 | 9/2015 | Balachandreswaran et al. |
| 9,226,106 | B1 | 12/2015 | Kommann |
| 9,319,834 | B2 | 4/2016 | Robert et al. |
| 9,352,216 | B2 | 5/2016 | Mullen |
| 9,398,404 | B2 | 7/2016 | Pierce et al. |
| 2002/0090985 | A1 | 7/2002 | Tochner et al. |
| 2003/0210228 | A1* | 11/2003 | Ebersole ............ G02B 27/017 345/157 |
| 2006/0105838 | A1 | 5/2006 | Mullen |
| 2008/0015024 | A1 | 1/2008 | Mullen |
| 2009/0227374 | A1* | 9/2009 | Tirpak ............ A63F 13/12 463/40 |
| 2013/0063432 | A1 | 3/2013 | Kaps et al. |
| 2013/0178257 | A1* | 7/2013 | Langseth ............ G06T 17/05 463/4 |
| 2013/0328927 | A1* | 12/2013 | Mount ............ G06T 19/006 345/633 |
| 2014/0172640 | A1* | 6/2014 | Argue ............ G06Q 30/0641 705/26.61 |
| 2014/0237578 | A1 | 8/2014 | Bryant et al. |
| 2016/0140868 | A1* | 5/2016 | Lovett ............ G09B 19/0053 434/118 |
| 2017/0176202 | A1* | 6/2017 | Anderson ............ G01C 21/3492 |
| 2017/0337476 | A1* | 11/2017 | Gordon ............ G06N 5/022 |
| 2018/0075694 | A1* | 3/2018 | Frolov ............ G07F 17/3218 |

OTHER PUBLICATIONS

Paul J. Otterstedt, List of IBM Patents or Patent Applications Treated As Related, Jun. 26, 2018, pp. 1-2.
Nist, "The Nist Definition of Cloud Computing". Special Publication 800-145. Sep. 2011, pp. 1-7.
Rutkin, "Pokémon Go away: Who owns the augmented reality we play in?" New Scientist (Jul. 14, 2016), pp. 1-3.
Statt, "This Android app is the best way to find pokemon on the go" The Verge (Jul. 27, 2016), pp. 1-3.
John E. Kelly III, "Computing, cognition, and the future of knowing", IBM Corp. Oct. 2015, pp. 1-11.

\* cited by examiner

LOCATION-BASED AUGMENTED REALITY GAME CONTROL

BACKGROUND

The present invention relates to the electrical, electronic and computer arts, and more specifically, to augmented reality gaming.

Augmented reality ("AR") gaming is a location-based form of interactive entertainment. A game player consents to having their location tracked by a mobile device that they use to play the game. While playing the game, the mobile device displays a real-time image of the game player's location sometimes overlaid with an image of one or more game items (e.g., characters, resources, or game locations). Using the mobile device, the game player interacts with the virtual game items that are "present" at the player's real world location. Thus, as an essential part of the game, the player transits between real world locations and spends time in particular locations interacting with the game. One important aspect of a location-based augmented reality games is "trust" about real world locations.

SUMMARY

Principles of the invention provide techniques for location-based augmented reality game control. In one aspect, an exemplary method provides for deterring augmented reality game players from intruding on undesirable locations (e.g., high risk locations, culturally sensitive locations, locations marked by property owners). The exemplary method includes obtaining a location of a mobile device using a first sensor of the mobile device and accessing a first locational database responsive to the location of the mobile device. The exemplary method further includes retrieving from the first locational database an augmented reality object; obtaining an indication that the location of the mobile device is an undesirable location; and modifying the augmented reality object responsive to the indication that the location of the mobile device is an undesirable location. The exemplary method also includes displaying the modified augmented reality object at a display of the mobile device.

An exemplary embodiment of the invention is a non-transitory computer readable medium embodying computer executable instructions which when executed by a processor of a mobile device cause the processor of the mobile device to perform the exemplary method.

Another exemplary embodiment of the invention is an apparatus that includes a memory; a display; at least a first sensor; and at least one processor, coupled to said memory, said first sensor, and said display. The at least one processor is operative to implement the exemplary method.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

Monitoring various events and activities about the user (e.g. user context), location, crowd pressure, etc., using data from mobile device sensors and other plurality of data sources and computing devices.

Facilitating feedback regarding a real-world location containing an augmented reality character or considered for such containing in the future by assessing concern or risk level of the location.

Modifying the augmented reality character or object and displaying the modified augmented reality object at a display of the mobile device based on the location of the mobile device is an undesirable location.

Detecting and predicting excessive and/or unhealthy gaming use by measuring the obsessive and excessive interaction or usage of augmented reality associated with negative life experiences such as distraction, anxiety and preoccupation.

These and other features and advantages of the present invention will become apparent from the following detailed description of illustrative embodiments thereof, which is to be read in connection with the accompanying drawings.

DETAILED DESCRIPTION

Figure 1:
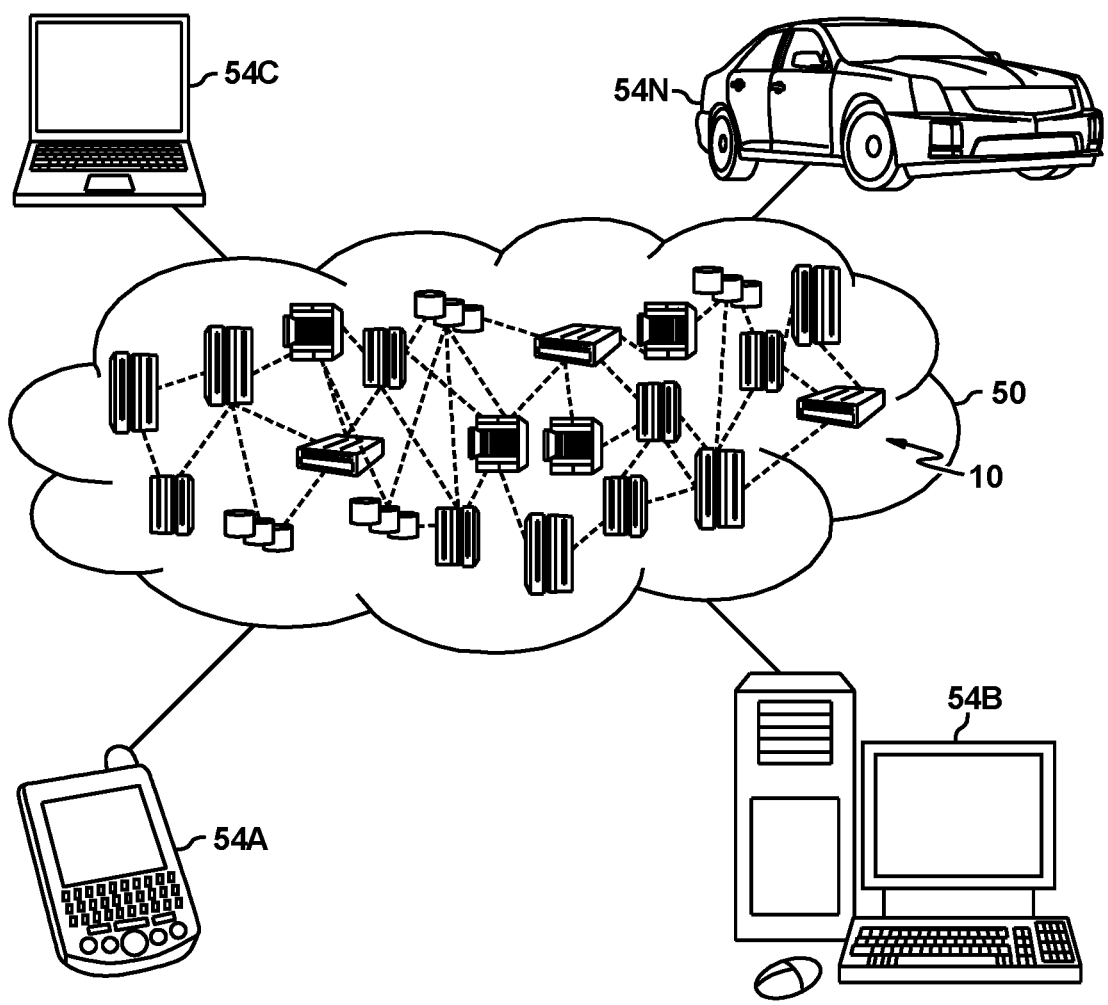
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
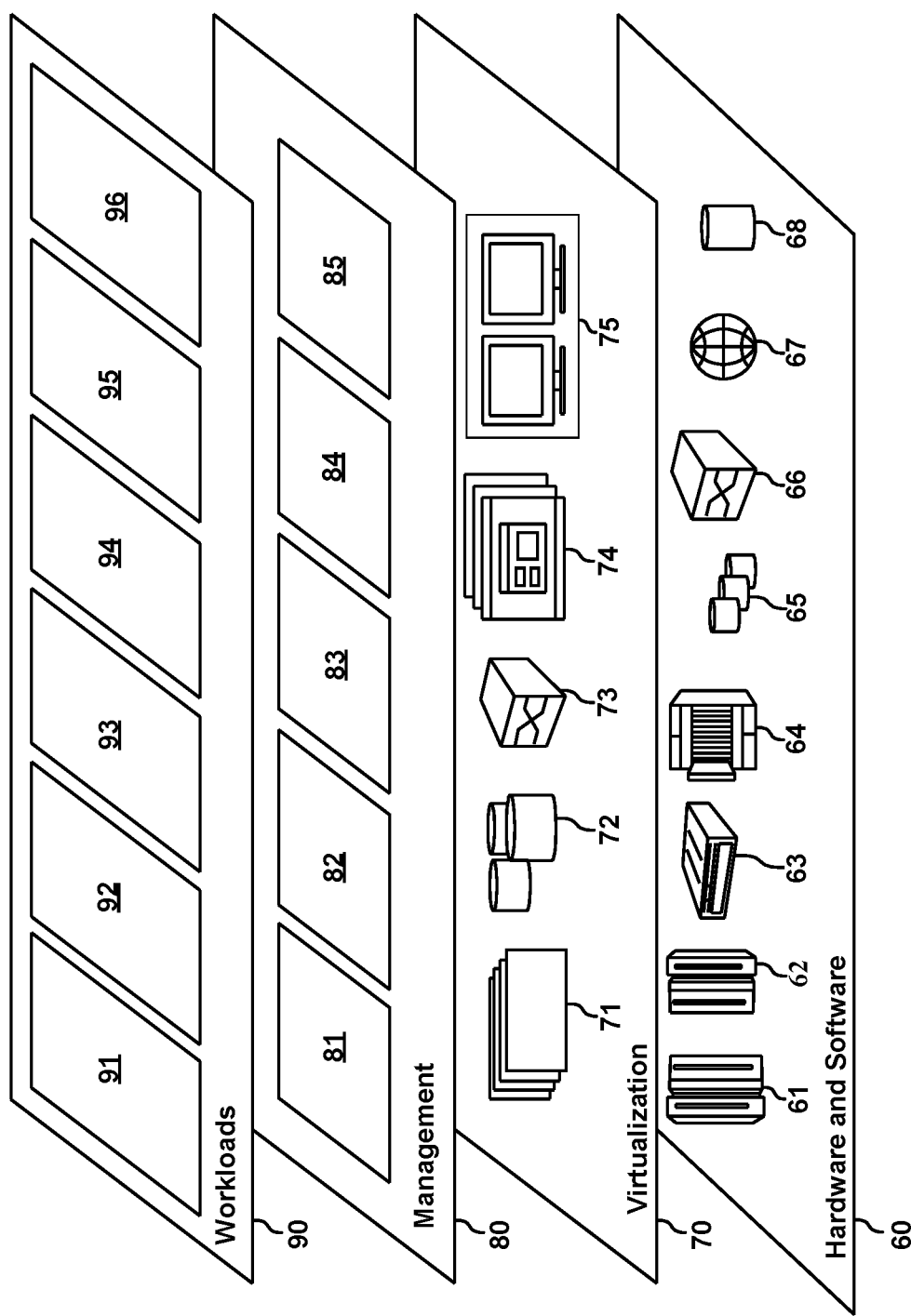
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and location-based augmented reality game control 96.

Figure 3:
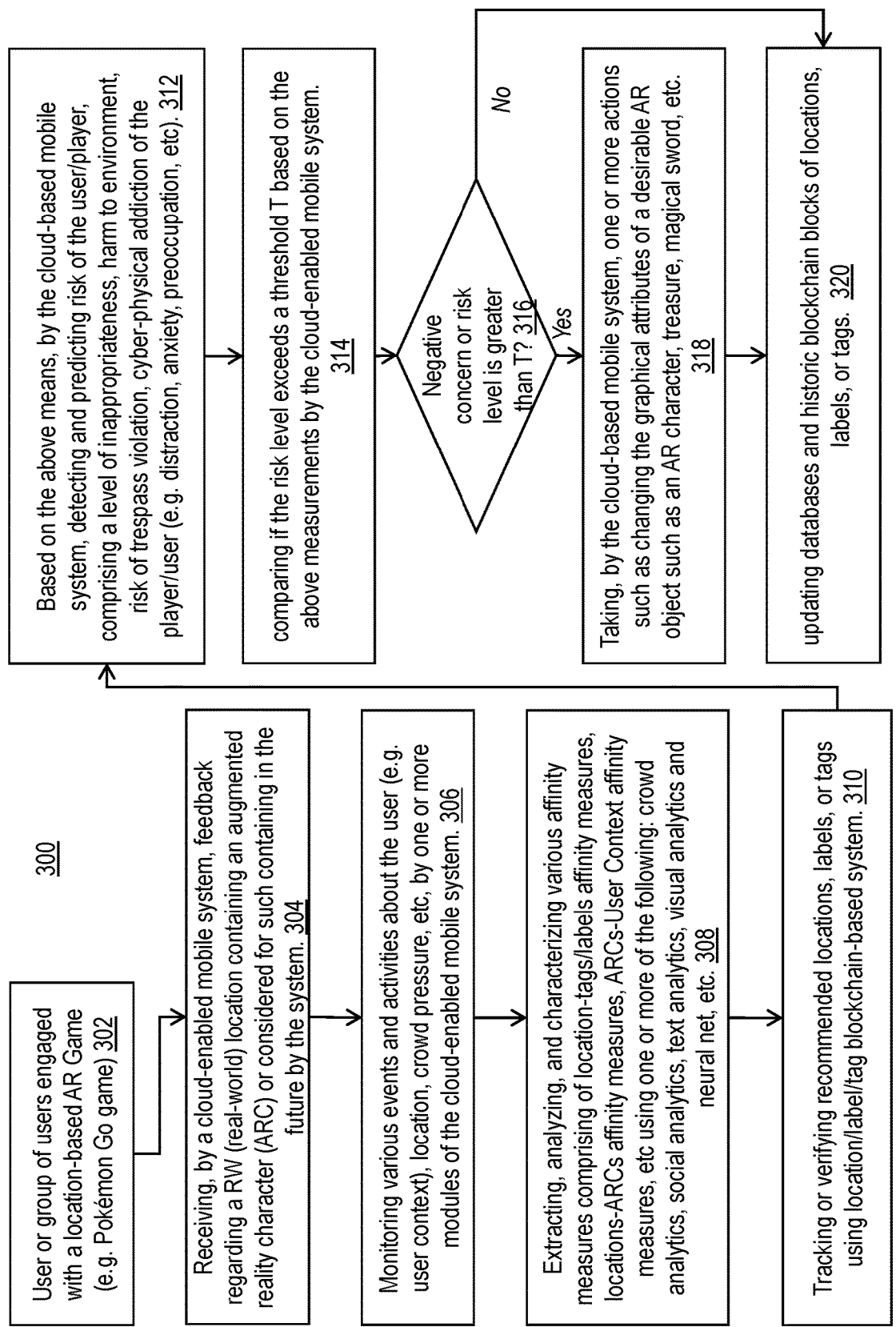
FIG. 3 depicts in flowchart form a method for location-based augmented reality game control, according to embodiments of the invention.

Referring to FIG. 3, a method 300 according to embodiments of the invention includes identifying 302 a user or group of users engaged with a location-based augmented reality ("AR") game. The method 300 also includes receiving 304, by a cloud-enabled mobile system, feedback regarding a real world ("RW") location associated with an AR object ("ARC") or considered for future association with an ARC. Additionally, the method 300 includes monitoring 306 various events and activities about the user or group of users (e.g. user context), location, crowd pressure, etc., by one or more modules of the cloud-enabled mobile system. The method 300 further includes extracting, analyzing, and characterizing 308 various affinity measures such as location-tags/labels affinity measures, locations-ARCs affinity measures, ARCs-User Context affinity measures, etc. Exemplary affinity measures include how often a location has been labelled as "safe" or "dangerous", how frequently a particular ARC spawns at a given location, how many times a user has collected a given ARC. The data for various affinity measures are obtained from mobile built-in sensors (e.g., accelerometer, gyroscope, GPS, camera sensor, audio sensor, touch sensor, temperature, etc.), other nearby computing or communication devices (e.g. Wifi, beacon, network tower, nearby user computing devices such as mobile phones of other players), and other data sources such as user electronic calendar, social media data (e.g. twitter, Facebook, etc.) and other crowdsourced public data to determine or infer the user cognitive and affective states, user profile and context, as well as to determine the profile of the location. Users may opt-in or opt-out of having various information used to generate the affinity measures. In a simplest exemplary embodiment, the user's location, which already is tracked as part of game play, is used to assess user context such as total time involved in game play, speed between game locations, etc. Various existing algorithms and learning techniques such as crowd analytics, social analytics, text analytics, and visual analytics can be trained and/or configured to compute the affinity measures, using data obtained from the various sources as mentioned above.

For example, contextual analysis of the phone/device usage (e.g., by detecting emergency situations from incoming text message sent, incoming tweets, incoming calls, incoming Facebook alerts, checking maps) may enable generating alerts or tips while at the same time making graphical changes to an AR object to deter game players from approaching an undesirable location.

Additionally, the method 300 may include capturing a live camera image of the real world, and determining whether there are image tags/IDs in the real world in the live camera image. Such tags (e.g. on real-world signs, on walls, on trees) may be used to moderate, control, or influence the ARC based on the needs of the stakeholders (e.g., supervisors of wildlife preserves, homeowners, hospitals) who have placed the tags (e.g. bar codes, QR codes, RFIDs, etc.). For example, real world locations (such as shops, restaurant, tourist events, safari animal activity sites, cemeteries) may use tags not only to ban or modify ARCs that would otherwise be generated by the AR game, but also to add special ARCs to their locations. The user may optionally opt-in to read these tags with their phones, because some users may want to reduce risk, be good citizens, etc. Alternatively, detecting and reading such tags may be made an integral feature of the AR game.

As noted, one important aspect of a location-based augmented reality games is "trust" about real world locations. Actors or users may maliciously profile a location for different purposes (e.g., misleading game players by falsifying the profile of a location where the ARC can be placed). Thus, it is important for the system to verify/validate any location related transaction. Accordingly, the method 300 includes tracking 310 or verifying recommended locations, labels, or tags using a location/label/tag blockchain-based system. The blockchain system securely tracks, stores, and maintains location related transactions along with other location metadata. A blockchain is a distributed database that maintains a continuously-growing list of data records hardened against tampering and revision. It consists of data structure blocks—which hold exclusively data in initial blockchain implementations, and both data and programs in some of the more recent implementations—with each block holding batches of individual transactions and the results of any blockchain executables. Each block contains a timestamp and information (e.g., a hash of a previous block) that links it to a previous block.

A blockchain is a distributed permissionless or permissioned ledger that maintains a continuously growing list of data records hardened against tampering and revision. It consists of data structure blocks—which hold exclusively data in initial blockchain implementations, and both data and programs in some of the more recent implementations—with each block holding batches of individual transactions and the results of any blockchain executables ("chaincode"). Each block contains a timestamp and information (e.g., a hash of a previous block) that links it to a previous block. Thus, a blockchain can serve as a public or proprietary network ledger of transactions committed by the users associated with the blockchain. Blockchain is peer-to-peer. Additionally, the blockchain resides not in a single server, but across a distributed network of computers. Accordingly, whenever new transactions occur, the peers of the distributed network authenticate the additions to the blockchain. Permissionless blockchain implementations allow any user to connect to the network, send new transactions to it, verify transactions, and create new blocks. In permissioned blockchain, only authorized users may sign and verify transactions. According to some implementations of permissioned blockchain, users initially can be authorized by hard-coded chaincode; thereafter the chaincode can be modified to authorize new users by consent of the existing authorized users.

Distributed recording and authentication provide substantial beneficial technical effects of blockchain technology. (1) The ability for independent nodes to converge on a consensus of the latest version of a large data set such as a ledger, even when the nodes are run anonymously, have poor interconnectivity and have operators who are dishonest or malicious. (2) The ability for any well-connected node to determine, with reasonable certainty, whether a transaction does or does not exist in the data set. (3) The ability for any node that creates a transaction to, after a confirmation period, determine with a reasonable level of certainty whether the transaction is valid, able to take place and become final (i.e., that no conflicting transactions were confirmed into the blockchain elsewhere that would invalidate the transaction, such as the same currency units "double-spent" somewhere else). (4) A prohibitively high cost to attempt to rewrite or alter transaction history. (5) Automated conflict resolution that ensures that conflicting transactions (such as two or more attempts to spend the same balance in different places) never become part of the confirmed data set.

In one embodiment, location tracking transactions associated with a stakeholder are compiled into a chain of location transaction blocks. The chain can be considered a chronicle of a location's historical profile through time. When a transaction is conducted (e.g. a location is created or updated), the corresponding location parameters (e.g., user information, tags, labels, time stamp) are sent to one or more validation components. The components establish a validity of the transaction and generate a new block. Once the new block has been calculated it can be appended to the location's historical profile blockchain. The system may further track a possible risk assessment (a multidimensional vector, with several dimensions of risk as discussed above). Computed location parameters/tags such as dangerous, safe, unknown, inappropriate, complaints filed, accidents, unlawful activity, culturally sensitive, etc. can be tracked and stored.

One example of added feature of a blockchain-implemented system is a "Lock In Attribution" feature, where the system can help create a permanent and unbreakable link between the history of the ARCs and player location pathways. That link—the record of historical profile of the location—can be verified and tracked. In addition, the feature "Gain Visibility" can help trace where and how ARCs placed, journey of the player, and locations visited. Our system may show all the profiles of the suggested ARC locations. According to another example, the feature "Certificate of Authenticity" may allow each registered actors/stakeholders (players, regulators, businesses, conservationists) associated with the game to have a COA, a built in unique cryptographic ID and the complete "ownership" game history. For example, the onboarding of suggested actors/stakeholders (players, regulators, businesses, conservationists) into the game may be logged in blockchain at the stakeholder's initial location and in the stakeholder's own game history. Each subsequent stakeholder action (e.g., collecting an ARC, labelling a location) then may be logged in blockchain both at the relevant location and in the stakeholder's own game history.

Responsive to the preceding steps, the method 300 also includes predicting 312 location-based risk of the user/player, taking into account a level of inappropriateness (e.g., solemn memorial location, health care facility, other culturally sensitive areas), risk of harm to environment, risk of trespass violation, history of unlawful activity or incidents involving AR players, accidents involving vehicular traffic, locations near train tracks or subway platforms, legal concerns related to trespassing, risks to wildlife or the environment, military bases, nursing homes, locations near Safari areas, wildlife areas, or game preserves, where dangerous wild animals can cause risk to player at a certain time of the day, or other features of a location that may render the location undesirable for AR gameplay.

The risk may also take into consideration risk of visiting a location (e.g. unknown places) based on predicted or forecasted of risk score using historical AR visits. Such related factors as time spent in area, distance walked in area, etc. may be considered—along with information related to other similar players in similar locations. The risk prediction/forecast may consider a number of warnings received in the last T minutes (e.g. prior 15 minutes) for the last K distance traveled (0.3 km), etc. The feedback is based on user/player reports, reports by property owners, reports by police or other officials, reports made by supervisors of wildlife preserves, etc. Such feedback may be registered by many means, including comments or text or image input using smartphones. It may also be supplied using more official means, such as forms supplied at a Web site. Geo-location-based services can be fetched from the Cloud such as between time T1 and T2 visiting a location L would expose the user to unlawful activity, possibility of a lion to come from the Safari region, etc. This can be useful for detecting the risk of accident, which may be a basis for generating informative amelioration action such as providing to the user useful/recommended tips via sound/text/graphics. For example, such system may detect that in 500 meters there will be a known dangerous intersection location L and the player is travelling to obtain an ARC at location L, please avoid visiting the place for the moment. Properties of unknown locations—as they relate to risk and inappropriateness and other parameters—can be learned, estimated, or inferred from nearby locations.

Further, the method 300 can alert users of risks pertinent to their particular cohorts (e.g. a diabetic kid who is losing track of time, thus placing himself at possible risk, when attempting to enter a corn field, far from any possible help) and/or excessive and/or unhealthy gaming behavior of the player/user (e.g. distraction, anxiety, preoccupation, etc.). Using, as mentioned above, data collected from mobile device built-in sensors (e.g., accelerometer, gyroscope, GPS, camera sensor, audio sensor, touch sensor, etc.) and other data sources, a custom pattern recognition and Natural Language Processing (NLP) module can be configured to analyze the speech, gait, facial expression, cognitive or affective states (e.g. distraction, anxiety) of the user. The custom module further may be configured to analyze environmental context (e.g. location, time of the day, etc.). From the user electronic calendar, social media activities and historical interactions across the player population, the user (pre)occupation can be inferred by using machine learning or statistical analysis techniques. Thus, risk prediction may take into consideration: user cohort (e.g., is the user alone or apparently playing/walking with others; approximate age; health, social, affective/cognitive context), location of cohort, etc. For example, a user may actually specify a desire to be protected in some way because the user has fallen in the past or been involved in an unlawful incident.

Further, the system and method 300 may comprise various learning modules (e.g. NLP) which may be embedded as part of the underlying AR game platform for verifying or regulating when and how to trigger or suggest amelioration actions. For example, the suggested amelioration actions may be triggered when a timer or progress bar has passed a risk threshold in a space of high dimensions that includes several dimensions of possible concern—wherein the said timer and progress bar is computed or learned in real-time, by instrumenting the player activities, locations of ARC, etc. The risks and concerns may be multidimensional in nature, with estimated components stored in a higher-dimensional array. A multidimensional risk array may contain entries about risk related to the user (derived from user cognitive or affective states, user context and cohort such as related to health status, etc.), risk related to the location (derived from location profile), etc. Another dimension can be a risk of combination of two or more players. A further dimension can be events and actions already took place as well as other event sequences that can lead to potential incidents. Another dimension can be whether it is a single entity or an entity that is part of a social network performing the action or exhibiting the suspicious behavior. Further, the level of destruction caused by other players or ARCs being placed in a location can be a dimension. In addition, the multidimensional array is dynamically updated as new risk is discovered and/or computed by the sensors and configured cognitive neural network module.

Generally, a cognitive neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. A cognitive neural network can implement supervised, unsupervised, or semi-supervised machine learning.

Thus, risk prediction can occur based on rules learned by the cognitive neural network from past transactions in the blockchain, for example, a pattern of many user movements combined with discrete results such as incident reports, complaints against users, etc. By running the learned rules on more recent patterns of user movements, it is possible for the cognitive neural network to identify potential risks to users with varying degrees of confidence.

According to another example of risk prediction, a news feed can be utilized to determine that the risk might be higher on a particular location at a day, week, or month, based on different activities or events occurring in the area, including protest, riot or holiday activities. Thus, the inputs for the risk array can be dynamic and can change (even significantly) over time. A risk analysis module uses the multidimensional array to generate a risk score for a given location, e.g., where the ARC is placed. If this risk level is higher than a specified threshold T, it may trigger the amelioration module.

By comparing 314 the location-based risk to a threshold T, the method 300 determines 316 whether to ameliorate 318 the risk by taking one or more actions. Amelioration actions may include removing the AR object; substituting a different (less valuable) AR object; or changing graphical attributes of the AR object (e.g., placing a veil or other graphic item on the object to indicate various sorts of risks or to suggest that AR players be quiet, avoid lingering, keep alert to danger). More severe amelioration actions might include shutting down the AR game app, switching off the mobile device, vibrating or actuating a flashing light of the mobile device. Another amelioration action might be sending alerts to other family members or close relatives or friends (obtained user's contact list) based ARC-User Context Affinity measures (e.g., emotionality destructed or anger about the ARC or location situation with a User of diabetes type 2).

By analyzing the context list (including contact tags such as family member, friends, etc.), frequency of calls, time of calls, social networking, the user family tree or social graph can be generated and updated. The mobile system can be configured with the family tree or social graph so that the system can look-up whom to alert runtime.

According to some implementations of the method 300, amelioration actions may be triggered only when crowd pressure (which is given as the local velocity variance multiplied by the local crowd density) or crowd density exceed a threshold. Crowd pressure is a useful risk indicator of possible impending stampede. Crowd pressure may be estimated based on monitoring locations of a plurality of mobile devices, for example, mobile devices that have the same AR game app installed.

After ameliorating 318 the risk, the method 300 proceeds to updating 320 databases and historic blockchain blocks of locations, labels, or tags. The historic events blockchain associated to a location may be analyzed, by validating feedback provided regarding the location safety, level of risk, etc., in order to prevent cheating or misleading a game player.

Given the discussion thus far, it will be appreciated that, in general terms, an exemplary method, according to an aspect of the invention, includes obtaining a location of a mobile device using a first sensor of the mobile device and accessing a first locational database responsive to the location of the mobile device. The exemplary method further includes retrieving from the first locational database an augmented reality object; obtaining an indication that the location of the mobile device is an undesirable location; and modifying the augmented reality object responsive to the indication that the location of the mobile device is an undesirable location. The exemplary method also includes displaying the modified augmented reality object at a display of the mobile device.

The augmented reality object may be modified by changing its appearance; by substituting a less desirable augmented reality object; or even by removing the augmented reality object from the display of the mobile device.

The indication that the location of the mobile device is an undesirable location may be obtained from the first locational database or from a second locational database, or may be obtained from a real world marker using a second sensor of the mobile device. Alternatively, the indication that the location of the mobile device is an undesirable location may be generated by the mobile device responsive to known characteristics of a user of the mobile device, or may be generated responsive to an estimate of crowd pressure at the location of the mobile device. For example, an estimate of crowd pressure may be obtained by monitoring at least one other mobile device.

According to certain implementations of the invention, an exemplary method may also include receiving feedback, via the mobile device, concerning the location of the mobile device; and updating the first locational database or a second locational database, responsive to the feedback, to indicate that the location of the mobile device is an undesirable location.

According to certain implementations of the invention, the modified augmented reality object may be displayed overlaid on a real world map.

An exemplary embodiment of the invention is a non-transitory computer readable medium embodying computer executable instructions which when executed by a processor of a mobile device cause the processor of the mobile device to perform any of the methods above discussed. According to certain embodiments, the computer executable instructions may include instructions which when executed by the processor of the mobile device cause the processor of the mobile device to perform the additional steps of monitoring at least one characteristic of a user of the mobile device; and generating an indication that the location of the mobile device is an undesirable location, responsive to the at least one characteristic of the user of the mobile device.

Another exemplary embodiment of the invention is an apparatus that includes a memory; a display; at least a first sensor; and at least one processor, coupled to said memory, said first sensor, and said display. The at least one processor is operative to implement any of the methods above discussed.

Figure 4:
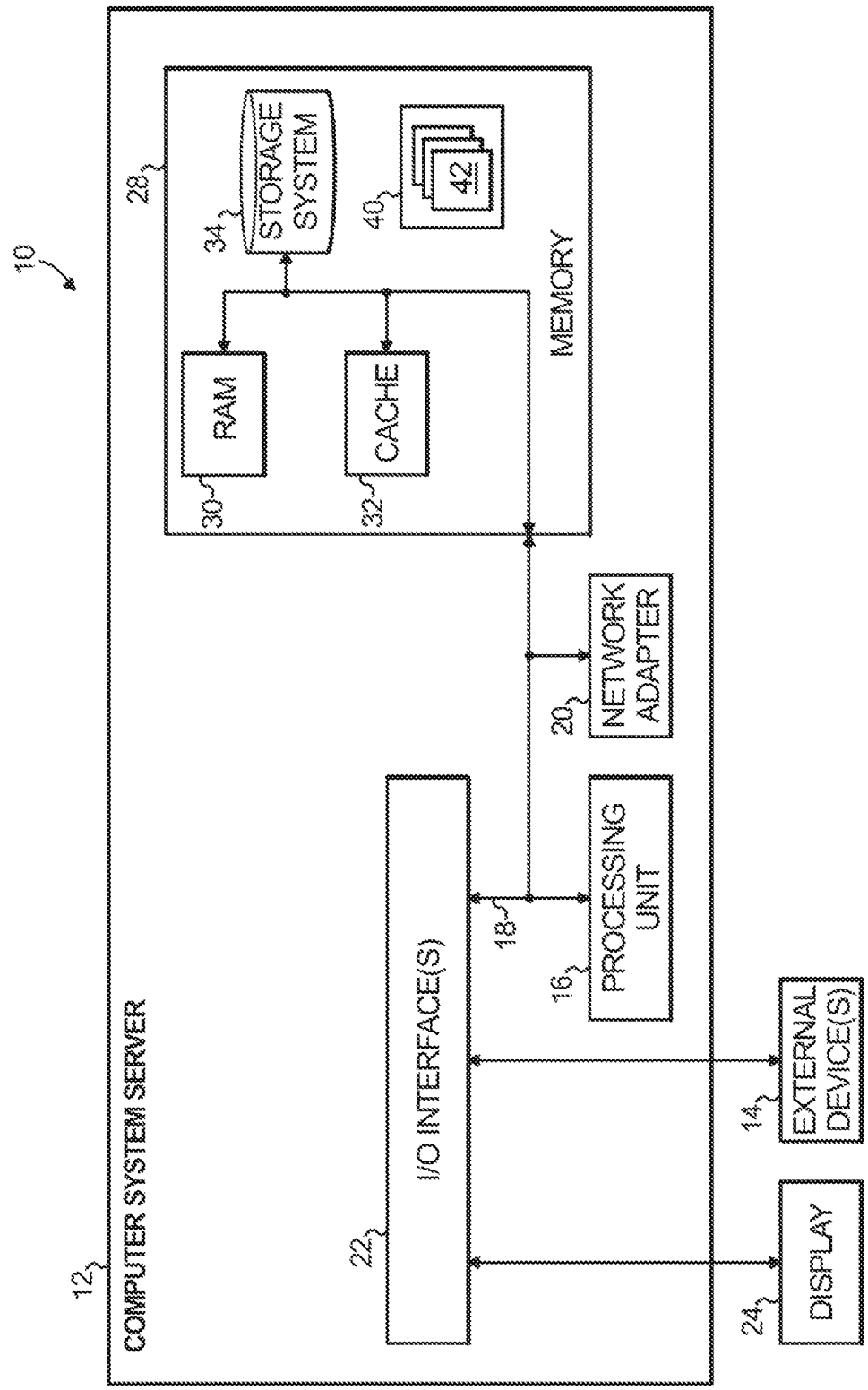
FIG. 4 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 4 depicts a computer system that may be useful in implementing one or more aspects and/or elements of the invention, also representative of a cloud computing node according to an embodiment of the present invention. Referring now to FIG. 4, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 4, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 4) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI). For example, implementations of the invention intercept and modify augmented reality object (character or item) code provided from an augmented reality game server, so as to alter the augmented reality object in a manner consistent with the purpose of the invention (deterring game players from intruding on undesirable locations).

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A non-transitory computer readable medium embodying computer executable instructions which when executed by a processor of a mobile device cause the processor of the mobile device to perform the method of:
   obtaining a location of the mobile device using a first sensor of the mobile device;
   accessing a first locational database responsive to the location of the mobile device;
   retrieving from the first locational database an augmented reality object;
   monitoring a cognitive state of a user of the mobile device, based on at least one of social media data, mobile built-in sensors, and the user's electronic calendar;
   generating an indication that the location of the mobile device is an undesirable location, in response to the user's cognitive state;
   modifying the augmented reality object responsive to the indication that the location of the mobile device is an undesirable location; and
   displaying the modified augmented reality object at a display of the mobile device.

2. The medium of claim 1 further embodying computer executable instructions which when executed by the processor of the mobile device cause the processor of the mobile device to perform the additional steps of:
   receiving feedback, via the mobile device, concerning a characteristic of the location of the mobile device; and updating the first locational database or a second locational database, responsive to the feedback, to indicate that the location of the mobile device is an undesirable location.

3. An apparatus comprising:
a memory;
a display;
at least a first sensor; and
at least one processor, coupled to said memory, said first sensor, and said display, and operative to implement a method comprising:
obtaining a location of the apparatus using the first sensor;
accessing a first locational database responsive to the location of the apparatus;
retrieving from the first locational database an augmented reality object;
determining a cognitive state of a user of the apparatus, based on at least one of social media data, mobile built-in sensors, and the user's electronic calendar;
generating an indication that the location of the apparatus is an undesirable location, in response to the user's cognitive state;
modifying the augmented reality object responsive to the indication that the location of the apparatus is an undesirable location; and
displaying the modified augmented reality object at the display of the apparatus.

* * * * *